(12) United States Patent
Kopelman et al.

(10) Patent No.: US 9,795,461 B2
(45) Date of Patent: Oct. 24, 2017

(54) ARCH EXPANDING APPLIANCE

(71) Applicant: Align Technology, Inc., San Jose, CA (US)

(72) Inventors: Avi Kopelman, Palo Alto, CA (US); Shiva Sambu, Milpitas, CA (US); Rene M. Sterental, Palo Alto, CA (US); Eric Kuo, San Jose, CA (US); Mauricio de Alencar Casa, São Paulo (BR)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/439,834

(22) Filed: Feb. 22, 2017

(65) Prior Publication Data

US 2017/0156821 A1 Jun. 8, 2017

Related U.S. Application Data

(63) Continuation of application No. 14/491,617, filed on Sep. 19, 2014, now Pat. No. 9,610,141.

(51) Int. Cl.
*A61C 3/00* (2006.01)
*A61C 7/10* (2006.01)
(Continued)

(52) U.S. Cl.
CPC ............. *A61C 7/10* (2013.01); *A61C 7/002* (2013.01); *A61C 7/08* (2013.01)

(58) Field of Classification Search
CPC .............. A61C 7/10; A61C 7/08; A61C 7/002
See application file for complete search history.

(56) References Cited

U.S. PATENT DOCUMENTS 4,433,956 A 2/1984 Witzig
4,983,334 A 1/1991 Adell
(Continued)

FOREIGN PATENT DOCUMENTS

JP 2007260158 A 10/2007
WO 0180762 A2 11/2001
(Continued)

OTHER PUBLICATIONS

International Search Report and Written Opinion from related PCT Patent Application No. PCT/IB2015/001697, dated Dec. 17, 2015, 16 pp.

*Primary Examiner* — Glenn Richman
(74) *Attorney, Agent, or Firm* — Brooks, Cameron & Huebsch, PLLC (57) ABSTRACT

The present disclosure provides method, systems, and devices for expanding arch of teeth. A device for expanding an arch of teeth of a patient can include a removable shell formed of a first material having a number of cavities formed therein. The number of cavities are shaped to receive teeth of a patient. A device for expanding an arch of teeth of a patient can include an arch element extending from the removable shell in a lingual direction and across an arch width of the removable shell. The arch element can be formed of the first material and a second material that is a different material than the first material, can be designed to expand an arch of the teeth of the patient, and can have a width specific to a stage of a treatment plan.

17 Claims, 7 Drawing Sheets

(51) Int. Cl.
   *A61C 7/08*     (2006.01)
   *A61C 7/00*     (2006.01)

(56) References Cited

U.S. PATENT DOCUMENTS

| | | | |
|---|---|---|---|
| 5,002,485 A | 3/1991 | Aagesen | |
| 5,692,894 A | 12/1997 | Schwartz et al. | |
| 5,769,631 A | 6/1998 | Williams | |
| 6,328,745 B1 | 12/2001 | Ascherman | |
| 6,499,995 B1 | 12/2002 | Schwartz | |
| 7,121,825 B2 * | 10/2006 | Chishti | A61C 7/00 433/6 |
| 7,192,273 B2 | 3/2007 | McSurdy, Jr. | |
| 7,458,810 B2 * | 12/2008 | Bergersen | A61C 7/08 433/6 |
| 7,500,851 B2 | 3/2009 | Williams | |
| 7,874,836 B2 | 1/2011 | McSurdy, Jr. | |
| 7,963,766 B2 * | 6/2011 | Cronauer | A61C 7/00 433/6 |
| 8,017,891 B2 | 9/2011 | Nevin | |
| 8,118,592 B2 | 2/2012 | Tortorici | |
| 8,201,560 B2 | 6/2012 | Dembro | |
| 8,465,280 B2 * | 6/2013 | Sachdeva | A61C 7/00 433/24 |
| 9,108,338 B2 | 8/2015 | Sirovskiy et al. | |
| 9,433,476 B2 * | 9/2016 | Khardekar | G06F 17/50 |
| 2004/0009449 A1 | 1/2004 | Mah et al. | |
| 2005/0186524 A1 | 8/2005 | Abolfathi et al. | |
| 2007/0178421 A1 | 8/2007 | McSurdy, Jr. | |
| 2012/0129117 A1 | 5/2012 | McCance | |
| 2014/0363778 A1 | 12/2014 | Parker | |

FOREIGN PATENT DOCUMENTS

| | | |
|---|---|---|
| WO | 03003932 A2 | 1/2003 |
| WO | 2006096558 A2 | 9/2006 |

* cited by examiner

```
┌─────────────────────────────────────────────────────────────────┐
│ FORMING A FIRST PORTION OF AN ARCH ELEMENT OF A MATERIAL USING  │
│ A DIGITAL MODEL OF A PALATE OF A PATIENT AND A DIGITAL MODEL OF │
│ A NUMBER OF TEETH OF THE PATIENT, WHEREIN THE FIRST PORTION     │──212
│ OF THE ARCH ELEMENT IS WIDER THAN AN ARCH WIDTH OF THE NUMBER   │
│ OF TEETH OF A FIRST JAW OF THE PATIENT, SPECIFIC TO A STAGE OF A│
│ TREATMENT PLAN, AND IS SHAPED TO SUBSTANTIALLY FOLLOW           │
│ CONTOURS OF THE PALATE OF THE PATIENT                           │
└─────────────────────────────────────────────────────────────────┘

┌─────────────────────────────────────────────────────────────────┐
│ FORMING A REMOVABLE SHELL OVER A SET OF MOLDED TEETH, WHEREIN   │
│ THE REMOVABLE SHELL INCLUDES: A NUMBER OF CAVITIES FORMED       │
│ THEREIN, WHEREIN THE NUMBER OF CAVITIES ARE SHAPED TO RECEIVE   │
│ THE NUMBER OF TEETH OF THE PATIENT, AND A SECOND PORTION OF     │
│ THE ARCH ELEMENT FORMED OF THE SAME MATERIAL AS THE NUMBER      │──214
│ OF CAVITIES, WHEREIN THE MATERIAL FORMING THE FIRST PORTION OF  │
│ THE ARCH ELEMENT IS MORE RIGID THAN THE MATERIAL FORMING THE    │
│ SECOND PORTION OF THE ARCH ELEMENT AND WHEREIN THE SECOND       │
│ PORTION IS THE SAME WIDTH AS THE FIRST PORTION OF THE ARCH ELEMENT│
└─────────────────────────────────────────────────────────────────┘

┌─────────────────────────────────────────────────────────────────┐
│ CONNECTING THE FIRST PORTION OF THE ARCH ELEMENT TO THE SECOND  │
│ PORTION OF THE ARCH ELEMENT TO FORM THE DENTAL APPLIANCE,       │
│ WHEREIN THE ARCH ELEMENT IS DESIGNED TO PROVIDE A FORCE TO AT   │──216
│ LEAST A PORTION OF THE NUMBER OF TEETH IN A FACIAL DIRECTION TO │
│ EXPAND THE ARCH OF TEETH OF THE FIRST JAW OF THE PATIENT        │
└─────────────────────────────────────────────────────────────────┘
```

ARCH EXPANDING APPLIANCE

PRIORITY INFORMATION

This application is a Continuation of U.S. application Ser. No. 14/491,617, filed Sep. 19, 2014, the entire contents of which are hereby incorporated by reference.

BACKGROUND

The present disclosure is related generally to the field of dental treatment. More particularly, the present disclosure is related to methods, systems, and devices for expanding an arch of a patient. Dental treatments may involve, for instance, restorative and/or orthodontic procedures.

Restorative procedures may be designed to implant a dental prosthesis (e.g., a crown, bridge inlay, onlay, veneer, etc.) intraorally in a patient. Orthodontic procedures may include repositioning misaligned teeth and/or changing bite configurations for improved cosmetic appearance and/or dental function. Orthodontic repositioning can be accomplished, for example, by applying controlled forces to one or more teeth over a period of time As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are lightweight and/or transparent to provide a set of appliances that can be used serially such that as the teeth move, a new appliance can be implemented to further move the teeth toward the desired goal.

In some instances, the width of a dental arch of a patient's upper dentition and/or and a width of a dental arch of a patient's lower dentition can be insufficient (e.g., too narrow) and on rare occasions, the width may be excessive (e.g., Brodie bite). A dental arch that is insufficient can result in malocclusions such as crossbite, crowding of teeth, impacted teeth, and/or the patient's smile may not be aesthetically pleasing in appearance. For instance, a patient's smile may be "narrow" resulting in a sunken appearance in the buccal corridors due to the inability to see the back teeth from the front view.

In certain types of front-to-back bite correction (e.g., Class II and Class III correction), a need for transverse width correction exists, without which the upper and lower arches will not be properly coordinated. For Class II correction, the upper needs to be expanded so that when the lower is advanced, the teeth in the buccal regions (typically the bicuspids and molars) are fitting together correctly in the buccal-lingual dimension. For Class III correction, the reverse is required, and the lower needs to be expanded since it is usually the one that has compensated for the Class III bite by constricting. When both Class II and Class III are corrected to a more ideal Class I bite, the respective compensations need to be undone, and a transverse width dimension of movement is necessary in addition to the anterior-to-posterior movement.

The width of a dental arch of a patient can be expanded, for instance, using an orthodontic appliance. The typical process for correcting a narrow appearance is palatal expansion. Currently available orthodontic appliances can include a permanent fixture that may be displeasing, both physically and aesthetically, to a patient. For example, currently available orthodontic appliances can include a jackscrew and/or other mechanism that is employed to deliver a horizontal stretching force to the molar teeth to split the upper jaw of the patient along the midpalatal suture. Such a mechanism typically spreads the left and right maxillary plates of the palate apart and then new bone material grows in between to fill the gap. As such, a large horizontal force, in many cases, is delivered by a professional and can cause discomfort and/or pain for a patient.

In some instances, the screw and/or other mechanism can be employed incrementally one or more times a day (e.g. 0.25 mm expansion twice a day—one activation in the morning and once at night). For example, a pinhole can be present in the orthodontic appliance and a patient can insert an activation key into the pinhole to incrementally increase a distance between portions of the orthodontic appliance. Such orthodontic appliances can be difficult for a patient to use, and often require assistance from another person (e.g., a parent) to turn the key. Not only are such appliances often not aesthetically pleasing, they often times interfere with the patient's speech, temporarily affect their ability to chew and/or swallow, and/or can be painful when activated. Adding to the challenges of such an appliance is the need to retain the expansion while the bone is filling into the suture, long after the active expansion has taken place. The active expansion process may be completed within 2 or 3 weeks' time, but the retention period can last around 6 months while waiting for the gap between the maxillary halves to fill in with new bony tissue.

DETAILED DESCRIPTION

As discussed above, the present disclosure provides methods, systems, and devices for expanding an arch of a patient. Generally, the expansion occurs during an orthodontic treatment which is a process of moving and reorienting teeth for functional and/or aesthetic purposes, although repositioning may be made for other purposes.

In some instances, an arch of a patient's teeth can be insufficient (e.g., narrow), and in rare occasions, too wide. An insufficient arch of a patient's teeth can cause overcrowding of a patient's teeth, impacted teeth, speech difficulty, breathing issues, and/or the smile of a patient can be aesthetically unpleasing. A narrow arch also prevents the anterior-posterior bite relationship from being corrected properly. An arch of teeth, as used herein, can include a curved row of teeth on a particular jaw of a patient. An insufficient arch can include an arch that has a width too narrow to support the row of teeth in a correct alignment, for instance. The arch width of a patient's teeth can be expanded, for instance, using an orthodontic appliance (e.g., a dental appliance).

Patients that are children or teenagers may have a maxilla where the midpalatal suture has not yet fused. Usually in the mid- to late-teens, the palatal suture fuses and the halves of the maxilla join together to become a single maxillary bone. The maxilla (e.g., the upper jaw) is a bone that is fixed to the skull. The mandible (e.g., lower jaw) is a bone that is attached to the skull by numerous muscles which power its movement. The mandible articulates at its posterior upward extremities with the temporal bone to form the jaw joint. The jaw joint is a loosely connected joint that accommodates the variety of movements of the mandible relative to the maxilla during biting and chewing. In correctly shaped and positioned jaws, the upper teeth occupy an arch that is wider than the arch comprising the lower teeth. In other words, the upper teeth are designed to be buccally positioned relative to the teeth in the lower jaw. Malocclusions such as crossbite occur when this normal arrangement is reversed and one or more of the upper teeth are positioned lingual to the teeth in the lower jaw.

A patient with an un-fused maxilla can for instance have their palate skeletally expanded. This is in contrast to dental expansion where the teeth are uprighted or moved within the boundaries of the jaw in which they are contained. With skeletal expansion, the underlying bone is moved and the teeth are moved along with the changes to the shape of the bone. Expanding a palate can, for instance, include splitting the left and right sides of the maxilla so that the teeth on the upper left side move as a single unit relative to the teeth on the right side. Because of this phenomenon, a gap between the top two front teeth can open up during the expansion process if they are not restrained from separating.

As discussed above, expansion of the palate, such as those methods performed prior to an orthodontic treatment involving braces and wires, includes having a treatment professional place an orthodontic appliance that may include anchoring bands, support bars, springs, and/or jack screws. The appliance is firmly affixed to the teeth at the anchor points and the springs or jackscrew applies forces on the teeth in order to move the underlying portions of the palate of the patient, thereby causing the arch of the patient's dentition to widen. To adjust the appliance and increase the amount of expansion, the patient and/or another person must insert a key into the pinhole and turn the key to increase the width of the orthodontic appliances. In some examples, prior approaches can include a removable appliance which contains a jackscrew expander that is activated with a pinhole key. These movements are primarily dental in nature, in that the teeth are usually tipped outward (buccally) and within the existing perimeter of the bone. After expanding the arch of the patient to the desired width (and sometimes overcorrecting in order to anticipate potential relapse towards the narrowness initially present), further orthodontic treatment can be performed to move and re-orientate the teeth of the patient. This type of additional orthodontic treatment can be done concurrently with the above discussed palate expansion technique, but often times, the alignment phase is performed after the expansion phase.

Further, palate expansion devices that are used primarily for skeletal expansion are typically temporarily anchored to the molars and/or pre-molars of the patient for the duration of the expansion and cannot be removed except by a dental professional because they are cemented into place. The forces that are applied to the molars and/or premolars are rather high in order to separate the suture, and therefore, the treatment can be uncomfortable to the patient due to the high pressure that is generated during the activation period. Once the suture splits, the majority of the pressure is relieved and subsequent activations in close proximity to the initial activation are not as uncomfortable.

In contrast, expanding an arch of a patient (whether skeletally with a fixed appliance or dentally with a removable appliance) according to embodiments of the present disclosure, can include utilizing a set of one or more appliances, such as positioners, retainers, and/or other removable appliances (e.g., clear plastic polymer shells and/or aligners) having a shell to be worn over the teeth of a patient and having an arch element thereon that is designed to expand an arch of teeth of the patient by moving the teeth of the patient to a wider position within the jaw. These appliances, in some embodiments may also expand the palate to a degree, but with a different degree of reliability than the palate expanders discussed above, since the expansion in a dental expansion device is much more gradual (on the order of 0.5 mm per month as opposed to 0.5 mm per day), and so the amount of skeletal versus dental expansion cannot be easily determined or distinguished.

For example, one or more appliance embodiments can include a removable shell formed of a first material having a number of cavities therein, wherein the number of cavities are shaped to receive teeth of the patient. These appliances are not fixed to the teeth of the patient and therefore can be removed by the patient for periods of time during treatment without aid from other people or intervention by a treatment professional.

In various embodiments of the present disclosure, an arch element can extend from the removable shell in a lingual direction and across at least a portion of the arch width of the removable shell. The arch width can be from molar to molar, from premolar to premolar, from canine to canine, or from any tooth on the left side to any tooth on the right side. The arch element can be formed of a first material and from a second material that is a different than the first material in at least one physical property. For example, the first material may be a polyurethane and the second material also be a polyurethane material with the same chemical formula, but of different hardness or rigidity due to greater crosslinking. Or, the first material can be of one chemical composition (e.g. polyurethane), and the second material of an entirely different chemical composition (e.g. polyvinyl chloride).

The arch element can have a width specific to a stage of a treatment plan and can be designed to expand an arch of the teeth of the patient to that specified width, which may be less than the full width in which that arch is to be expanded (i.e., the arch expansion can be incrementally accomplished by expanding the arch a little at a time over the use of several differently designed sequential dental appliances). Or the arch may be over-expanded to compensate for incomplete biological response to the desired outcome, where the actual width of the teeth is less than the width programmed or built into the stage(s) of the treatment plan.

In some embodiments, the second material can include, for instance, a more rigid material than the first material designed to provide greater resistance and/or force in a horizontal direction (i.e., transverse direction) against the posterior teeth (e.g., molars and bicuspids) of the arch of the patient. In various embodiments, this second material can be designed to impart force to the molars and/or other teeth on the jaw of the patient in order to either help preserve or change the transverse dimensions of the arch. Additionally, in some embodiments, with the use of appliances on the upper and lower jaws, the force can be imparted to parts of the opposing jaw (e.g., teeth, jaw bone, etc.).

The expansion of an arch of teeth in the patient can be used to treat malocclusions such as crossbites, sagittal problems, crowding, and/or to help prevent or resolve impacted teeth, in various embodiments. The transverse support elements can be designed to not interfere with the shells of the dental appliance. In this manner, a dental appliance in accordance with embodiments of the present disclosure can be used to concurrently expand or constrict an arch of the patient while repositioning a number of teeth of the patient.

As discussed above, in some embodiments, a plurality of appliances can be worn by a patient successively to achieve gradual expansion (or constriction) of the arch of teeth in the patient. For instance, each of a plurality of dental appliances can include an incrementally wider width to expand the arch of the patient in incremental distances. In some such embodiments, since this arch expansion technique can be accomplished concurrently with other orthodontic treatments, the arch expansion can be accomplished over a series of appliances that will be utilized over a period of less than one year to multiple years, thereby making any pain and/or discomfort of the patient more consistent and less arbitrary without prolonging the overall time for orthodontic treatment.

In some embodiments, an appliance can be formed using a thermoforming process. For instance, a first portion of an arch element can be formed of a material using a virtual model of the palate of the patient and a virtual model of a number of teeth of the patient.

The first portion of the arch element can be wider than the arch width of the number of teeth of the first jaw of the patient and can be shaped to substantially follow contours of the palate of the patient. For expansion, this difference in the width will facilitate the movement of the arch outward toward the wider position of the arch element.

A removable shell can be formed over a set of molded teeth. The removable shell can include a number of cavities formed therein and shaped to receive the number of teeth of patient and a second portion of the arch element. The second portion of the arch element can be formed of the same material as the removable shell and can include the same width as the first portion of the arch element.

The first portion of the arch element and the second portion of the arch element can, for example, be connected to form the dental appliance. The first portion and second portion can be connected, in accordance with various embodiments of the present disclosure, by thermoforming the removable shell over the set of molded teeth with the first portion of the arch element placed within the set of molded teeth (e.g., encapsulated), by fusing the two materials together (e.g., ultrasonic welding), by adhering the first portion and the second portion using an agent subsequent to forming the first portion and the removable shell, and/or by adding a number of features to the first portion of the arch element (e.g., as discussed further herein). In this manner, a dental appliance can be formed that has two distinct material properties, but is unitary in nature (e.g., forms a single body that can be used by the patient even though it is formed of two materials). Such embodiments, are discussed with regard to the embodiments illustrated in the figures and discussed below.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1, and a similar element may be referenced as 304 in FIG. 3. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

Figure 1:
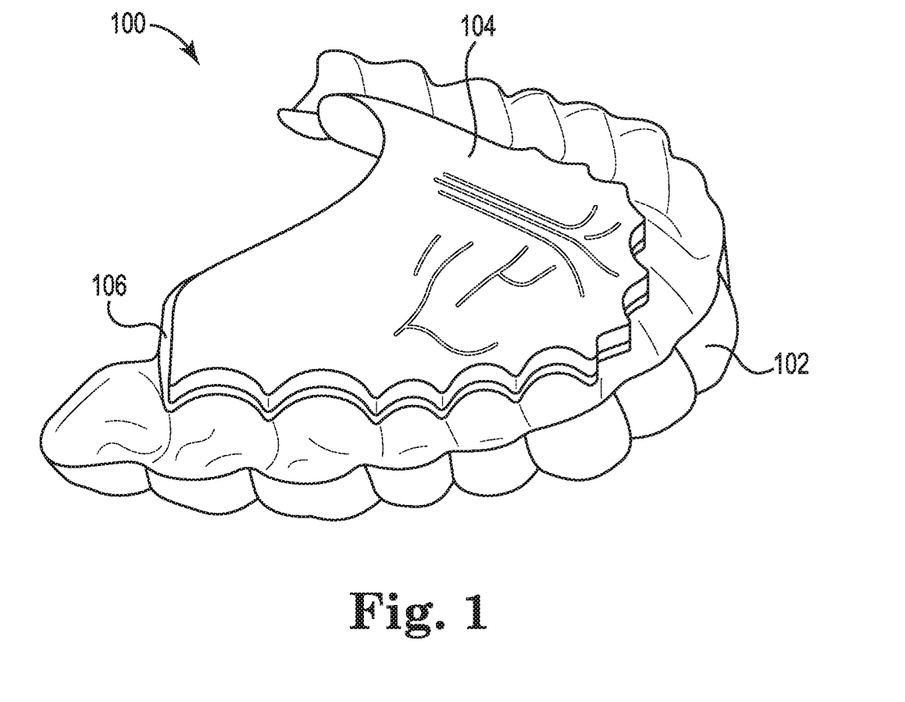
FIG. 1 illustrates an example of an appliance according to a number of embodiments of the present disclosure.

FIG. 1 illustrates an example of an appliance 100 according to a number of embodiments of the present disclosure. The appliance 100, illustrated in the embodiment of FIG. 1, can include an upper dentition appliance (e.g., an appliance placed on the upper jaw of the patient). An upper jaw can include a maxilla and can include a number of teeth of a patient's upper dentition. The lower jaw can include a mandible and can include a number of teeth of the patient's lower dentition.

Appliances can include any positioners, retainers, and/or other removable dental appliances for finishing and maintaining teeth positioning in connection with a dental treatment. These appliances may be utilized by the treatment professional in performing a treatment plan. For example, a treatment plan can include the use of a set of appliances, created according to models described herein. Appliances, in some embodiments, can include flexible dental appliances which serve, in part, as a prosthesis for esthetics and/or dental function.

An appliance can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth present in the upper and/or lower jaw. The shell can include an interior surface (e.g., adjacent to a surface of the teeth place therein) and an exterior surface. The interior surface is configured to receive and a apply forces to the teeth therein to reposition a number of teeth of the patient, for example.

In accordance with some embodiments of the present disclosure, the appliance 100 can include a removable shell 102 formed of a first material having a number of cavities formed therein. As discussed above, the number of cavities can be shaped to receive teeth of the patient.

The appliance 100 can include an arch element extending from the removable shell 102 in a lingual direction and across an arch width of the removable shell 102. The arch width of the removable shell 102, as used herein, is a space between the cavities of the removable shell 102. For instance, the arch element can expand across a surface of the mouth of the patient when the dental appliance 100 is placed over the teeth of the patient. The surface of the mouth can include, for instance, a palate and/or floor of the mouth.

The arch element, as illustrated by FIG. 1, can be formed of the first material 106 and a second material 104 that is different than the first material 106. The first material 106 can include the material that the removable shell 102 is formed of.

As discussed above, the arch element can be designed to expand an arch of teeth of the patient. For instance, the width of the arch element can be wider than the actual arch width of the teeth of the patient in order to define the desired arch width incremental target for the teeth. An arch width of the teeth of the patient can include a distance between teeth of the left posterior side of the patient's dentition and teeth of the right posterior side of the patient's dentition. As an example, the arch element can be 0.25 millimeters wider than the arch width of the teeth of the patient.

The second material 104 can be more rigid than the first material 106. For instance, the rigidity of the second material 104 can apply a force to at least a portion of the number of teeth in a transverse direction (e.g., horizontal direction) to expand the arch of teeth of the patient.

In some embodiments, the first material 106 of the arch element can form a first layer and the second material 104 of the arch element can form a second layer. The first layer of the first material 106 can be formed integrally with and of a same material as the removable shell 102, for instance. The second layer of the second material 104 can be formed in a separate process and attached to the first layer of the first material 106, for example (e.g., as discussed further herein).

In some embodiments, the arch element can follow contours of a surface of the mouth of the patient when the appliance 100 is placed over the teeth of the patient. For example, the second material 104 (e.g., the second layer of the second material 104) and/or the first material 106 (e.g., the first layer of the first material 106) can be shaped to substantially follow the contours of the palate of the patient. This can be accomplished, for example, by taking a mold or scan of the surface of the palate of the patient and then forming the surface of arch element to substantially match the mold/scan surface (i.e., the surface may not be identical, as the arch element may be designed to be wider as discussed above and therefore is not an identical copy of the mold/scan surface, and therefore may substantially match, but not be identical). The contours of the palate in the appliance may be interpolated in anticipation of a stretching of the tissues during the expansion, in order to better accommodate the seating of the appliance in the patient's mouth. In other words, the shape of the appliance is designed to include an expected stretching of the patient's palatal or lower lingual tissues during dental expansion, and not just a movement of the teeth.

In some embodiments, the first material 106, can be adjacent to and/or in contact with a tongue of the patient. The second material 104 can, for example, be adjacent to and/or in contact with a surface of the patient's mouth (e.g., the palate and/or floor of the patient's mouth). In this manner, the first material and second material form a layered construction.

The appliance 100 can be used for repositioning the number of teeth of the patient concurrently with expansion of the arch of teeth of the patient utilizing the arch element. The expansion of the arch of teeth can include movement of posterior teeth (e.g., molars) and/or other teeth of the arch of the patient in a transverse direction and/or stretching of the maxillary suture of the patient (e.g., separates the maxillary halves in the region of the suture), along with a stretching of the surrounding soft tissues (e.g., the palatal gingiva) during the expansion.

The simultaneous treatment of misalignment of a patient's dental arch (e.g., insufficient dental arch width) in conjunction with teeth alignment issues (e.g., rotation, tipping, etc.) can shorten treatments times when compared to current linear two-phase treatment protocols that first treat the misalignment of a patient's dental arch followed by treatment of misalignment of the patient's teeth. That is, the arch element can, in accordance with a number of embodiments, avoid and/or not interfere with engagement of the removable shell 102 with the teeth therein and thereby allow for correction of various tooth misalignment issues during the arch expansion process so that both arch expansion and alignment correction occurs in tandem rather than as separate phases.

Although the present embodiment of FIG. 1 illustrates an appliance for an upper dentition of a patient, embodiments are not so limited. Appliances, in accordance with some embodiments, can include an appliance for a lower dentition of a patient and/or an appliance for an upper dentition and a lower dentition. In some such embodiments, the arch element extending from a surface of an appliance for a lower dentition can substantially follow the contours of a portion of the floor of the patient's mouth. While the lower arch (i.e., mandible) does not contain a suture that can be split as the upper arch does, the same principles of appliance design described herein may be applied even in the lower in order impart greater transverse stability and/or force through the lower arch appliance to more effectively deliver transverse forces to the lower dentition for dental expansion purposes. In some such embodiments, since a generally horizontal span across the bottom of the patient's mouth may not be suitable for positioning of an arch element (e.g., because the tongue is in the way), an appliance of the present disclosure may include reinforced portions of the dental appliance that impart forces to help dentally expand the lower arch of the patient. For example, a portion of the arch element may be positioned in front of the tongue of the patient or in close proximity to the tongue in order to impart a horizontal force and the shell may be designed to transfer or redirect the resulting anterior force generated by the tongue towards the back portion of the jaw of the patient (e.g., closer to the molars).

In some embodiments, a first appliance can be placed over the upper dentition and a second appliance can be placed over the lower dentition of the patient. The first appliance and the second appliance can each have an arch element. The arch element of the first appliance and the arch element of the second appliance can expand the dental arch of the upper dentition and the dental arch of the lower dentition, respectively, to the same degree. Or in the case of Class II or Class III correction where a disproportionate amount of expansion/constriction is needed, the amounts can be coordinated so that the expansion targeted is suitable for the desired amount of anterior-posterior bite change.

In some embodiments of the present disclosure, the appliance 100 can be a portion of a treatment plan. For instance, the treatment plan can include a series of appliances designed to incrementally implement a treatment plan. Each of the series of appliances can be a stage of the incremental treatment plan, for instance. The series can be used for treating misalignment of teeth of a patient and/or misalignment of one or more arches of teeth of the patient. In some such embodiments, one arch can be expanded while the other arch is not expanded or both arches can be expanded simultaneously. Or one arch can be expanded while the other one is constricted.

For instance, a first appliance, of a series of appliances designed to incrementally implement a treatment plan can comprise a first shell formed of a first material having a plurality of cavities therein designed to receive teeth of a first jaw. The first appliance can include a first arch element formed of a first layer of the first material and a second layer of the second material different than the first material. The first arch element can extend from the first shell in a lingual direction and across an arch width of the first shell. For instance, the first arch element can have a first width specific to a first stage of the treatment plan and/or can be designed to expand an arch of the teeth of the patient.

A second appliance, of the series of appliances, can comprise a second shell having a plurality of cavities therein designed to receive teeth of the first jaw. The second appliance can include a second arch element. For example, the second arch element can have a second width specific to a second stage of the treatment plan. The second width can be wider than the first width. For instance, the second width can include an incremental increase in width as compared to the first width. The successive incremental increase in the arch width of the appliances corresponds to the desired gradual increase in the actual physical arch of the patient.

In accordance with some embodiments of the present disclosure, the series of appliances can include a third appliance. The third appliance can include a third shell having a plurality of cavities therein designed to receive teeth of the second jaw (e.g., the lower jaw). For instance, the third appliance can include a third arch element designed to expand the arch of teeth of the patient. The third arch element can have a third width specific to the first stage of the treatment plan.

In such an embodiment, the first appliance and third appliance can be for a first stage of the treatment plan. For instance, a patient can place the first appliance over the teeth of the first jaw (e.g., upper jaw) and can place the third appliance over the teeth of the second jaw (e.g., lower jaw). The first arch element of the first appliance and the third arch element of the third appliance can be designed to expand the arch of teeth of the first jaw and the arch of teeth of the second jaw to a same degree (e.g., equal distance) based on the first width and the second width. Equal distance in expansion amount is desirable if the upper and lower arches are already in good coordination and no front-to-back change in the bite is desired or planned.

In various embodiments, the series of appliances can include a fourth appliance. The fourth appliance can include a fourth shell having a plurality of cavities therein designed to receive teeth of the first jaw. The fourth appliance may not include an arch element and/or can include a fourth arch element, for example.

Although the present embodiments illustrate two stages of a treatment plan, embodiments in accordance with the present disclosure are not so limited. Treatment plans can include a variety of number of stages, including more or less than two treatment stages. At least a portion of the stages can include treatment for gradual expansion of an arch of teeth of a patient. Alternatively and/or in addition, one or more of the stages may not include arch elements, in various embodiments.

Figure 2:
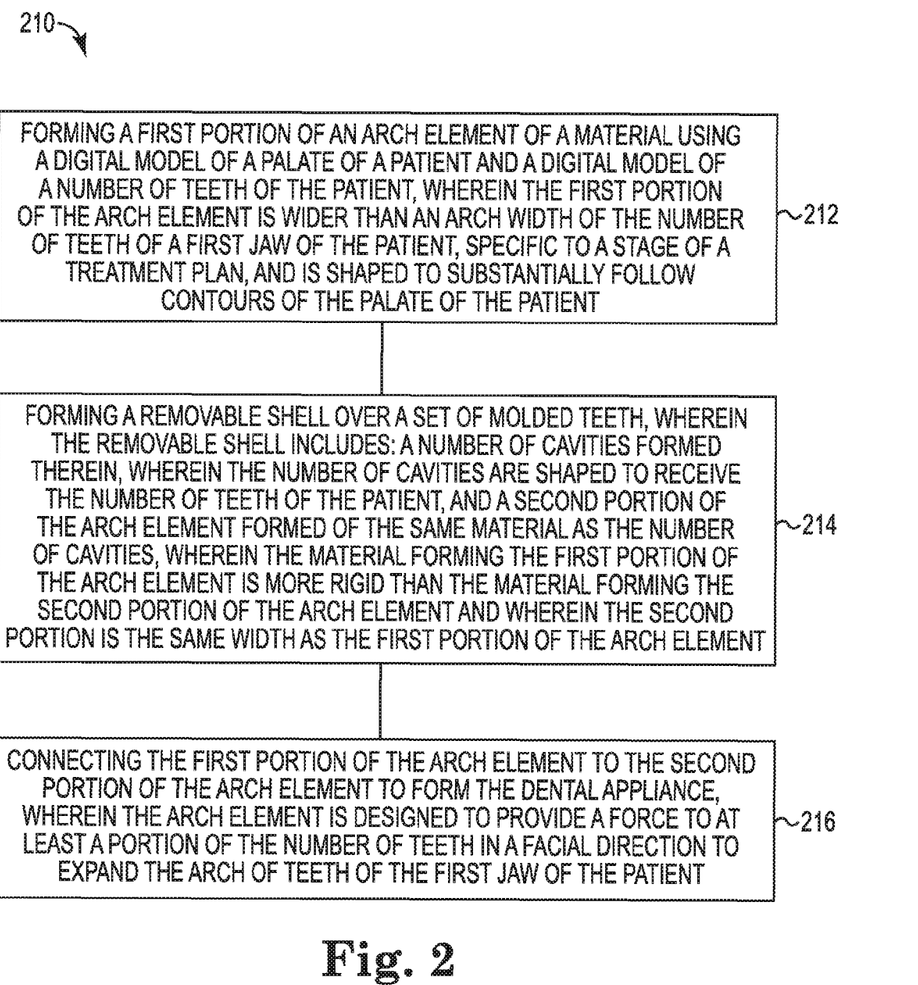
FIG. 2 illustrates an example of a method for forming a dental appliance according to a number of embodiments of the present disclosure.

FIG. 2 illustrates an example of a method 210 for forming a dental appliance according to a number of embodiments of the present disclosure. The method 210 can be utilized to form an appliance 100, as illustrated in the embodiment of FIG. 1.

At block 212, the method 210 can include forming a first portion of an arch element of a material using a virtual model of a palate of a patient and a virtual model of a number of teeth of the patient. The first portion of the arch element can be wider than an arch width of the number of teeth of the first jaw of the patient, specific to a stage of a treatment plan, and is shaped to substantially follow contours of the palate of the patient (that may also include modeling of anticipated changes to the palatal contours due to tissue stretching), for instance.

The palatal contours in the model can also be specifically raised in a vertical direction so that any appliance which is formed over the model is slightly raised in comparison to the actual contours of the palate. In other words, a slight gap between the actual palate and the palatal coverage portion of the appliance can be designed to be present. This gap allows the transverse benefits of the appliance design to be in effect while not necessarily requiring an exact fit of the appliance to the contours of the tissue. A slight offset in the vertical dimension minimizes any disruption in speech, swallowing, or feel due to changes in tongue position that may result in the alteration. More importantly, intentionally raising the vertical dimension of only the palatal tissue regions has the benefit of not needing perfect modeling of any non-linear stretching that might take place in the tissue; this greatly reduces the risk of uncomfortable pressure spots and sores caused by the appliance. Having to relieve pressure spots in the appliance can be very time consuming for the doctor, and if the appliance is thin to begin with, such adjustments can lead to weakened areas in the appliance.

A virtual model of a number of teeth of the patient can, for example, include an initial virtual dental model and/or an intermediate virtual dental model. A virtual model of the palate (and/or other tissue surfaces of the patient's mouth) can include the contours of the palate. In some embodiments, the virtual model of the palate and the virtual model of the number of teeth can include a single virtual model and/or two separate virtual models.

The first portion of the arch element can be formed by a rapid prototyping process, such as, for example, by a Computer-aided manufacturing (CAM) milling, stereolithography (i.e., 3-D printing), and/or photolithography. The first portion of the arch element can be shaped to fit between the arch of the first jaw of the patient while being sized to be wider than the arch width of the number of teeth of the first jaw of the patient. The flexibility of the appliance is such that it can be compressed in the transverse direction during seating in order to activate the expansion force. This force then gets released and directed towards the teeth, soft tissues, and/or jaw bone when then the appliance is seated in the mouth. In some embodiments, the first portion can be shaped to substantially follow contours of the palate of the patient using the virtual model of the palate. Alternatively and/or in addition, the first portion can be shaped to substantially follow contours of the floor of the mouth of the patient using a virtual model of the floor of the mouth.

At block 214, the method 210 can include forming a removable shell over a set of molded teeth. The removable shell can include a number of cavities formed therein, wherein the number of cavities are shaped to receive the number of teeth of the patient. In various embodiments, the removable shell can include a second portion of the arch element formed of the same material as the number of cavities. The second portion of the arch element can be formed integrally with and/or during a same process as the number of cavities, for instance.

The material forming the first portion of the arch element can be more rigid than the material forming the second portion of the arch element, for instance. In some embodiments, the second portion of the arch element can include the same width as the first portion of the arch element.

Alternatively and/or in addition, the first portion of the arch element can be designed to be adjacent to and/or in contact with a surface of the patient's mouth (e.g., the palate and/or floor of the patient's mouth) when the dental appliance is placed over the teeth of the patient. The second portion of the arch element can be designed to be adjacent to and/or in contact with a tongue of the patient when the dental appliance is placed over the teeth of the patient.

The dental appliance can be made, for example, by thermoforming a piece of plastic over a physical dental model. The physical dental model, for instance, can represent an incremental position to which a patient's teeth are to be moved. This desired position of the patient's teeth includes any underlying desired changes to the skeletal structure which holds the teeth in place. The physical dental models can be manufactured by downloading a Computer-aided Design (CAD) virtual dental model file into a rapid prototyping process, such as, for example, a Computer-aided manufacturing (CAM) milling, stereolithography (e.g., 3-D printing), and/or photolithography. The virtual dental model can be hollowed out or "shelled" before it is sent for manufacturing to save on material cost if printed, for example.

The dental model (e.g., set of molded teeth) can be created from a virtual model of a number of teeth of a patient. A dental model can be formed in accordance with a unique treatment file that identifies a patient, a stage of a treatment plan, the virtual model of the number of teeth, and/or whether the dental model is of the upper and/or lower dental arch.

In some embodiments, a treatment file can be accessed by a rapid prototyping apparatus machine, such as a SLA or printing, to form and/or create the dental model. The result of the dental model can include a set of molded teeth (e.g., a physical set of molded teeth). The set of molded teeth can include at least a replica of the number of teeth of the patient. The dental model can be used to make a dental appliance, for example, by creating a negative impression of the dental model using polymeric sheets of material and vacuum forming heated sheets of the polymer over the dental model, as discussed above.

For instance, a dental appliance can be created by layering a thermoformable sheet of material and/or multiple sheets of one or more materials over the dental model. The materials can include at least one polymeric material, for instance. Generally, the dental appliance is produced and/or formed by heating the polymeric thermoformable sheet and vacuum or pressure forming the sheet over the dental model (i.e., over a number of the teeth in the mold). The shape of the sheet of material can be designed to intentionally vary in thickness in some portions of the sheet (beyond natural variations in thickness during the shaping process) as it conforms to the mold shape. A dental appliance can, for example, include a negative impression of the dental model. The appliance and/or parts thereof may be transparent, semi-transparent, or opaque in such a way as to emulate a natural tooth shade.

At block 216, the method 210 can include connecting the first portion of the arch element to the second portion of the arch element to form the dental appliance. The arch element can, for example, be designed to provide a force to at least a portion of the number of teeth in a transverse direction to expand the arch of the teeth of the first jaw of the patient.

The first portion of the arch element and the second portion of the arch element can be connected in a variety of ways, in accordance with some embodiments of the present disclosure. For instance, the first portion of the arch element can be connected to the second portion of the arch element by thermoforming the removable shell over the set of molded teeth with the first portion of the arch element placed within the set of molded teeth (i.e., encapsulated by). An agent (e.g., a binding material) can be added to connect the first portion of the arch element to the second portion of the arch element created by thermoforming the removable shell. The first and second portions may also be secured to each other through ultrasonic welding or other techniques that allow adhesion without the need for an intermediary substrate such as a solvent or adhesive.

In accordance with some embodiments of the present disclosure, the first portion of the arch element can be connected to the second portion of the arch element by adhering the first portion and the second portion subsequent to forming the first portion of the arch element and the removable shell. In some embodiments, an agent can be utilized to cause the first portion of the arch element to adhere to the second portion of the arch element, however, in some embodiments, multiple materials used to form the first portion and second portion may be bonded without the use of an agent (e.g. ultrasonic welding, laser spot welding). The first portion can also be cured into place in direct contact with the dental model (e.g. a liquid resin such as polyacrylic painted onto the model and subsequently hardened through chemical or light cure) and then joined to the second material which is thermoformed over the first material to create an adherent bond between the two materials.

In various embodiments, the first portion can include a number of features (e.g., as discussed further herein). Connecting the first portion to the second portion of the arch element can include thermoforming the removable shell over the set of molded teeth with the first portion of the arch element placed within the set of molded teeth. The thermoformed material (i.e., the material the removable shell is formed of) can surround the number of features of the first portion of the arch element to connect the first portion to the second portion of the arch element.

Figure 3:
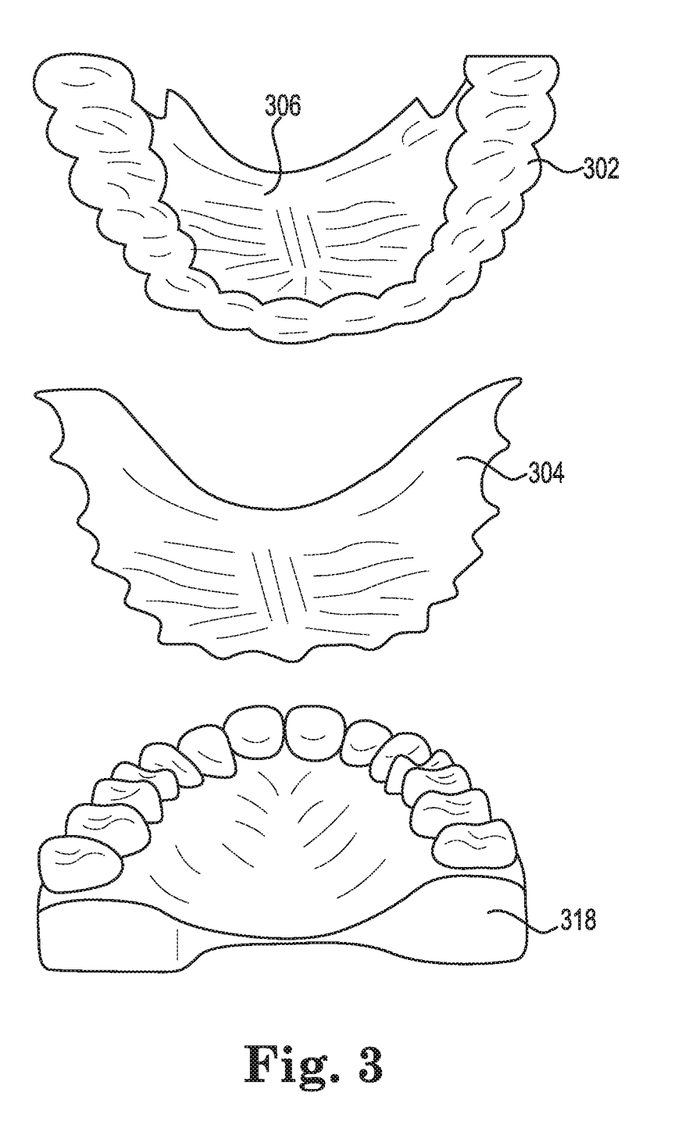
FIG. 3 illustrates an example of a process for forming a dental appliance according to a number of embodiments of the present disclosure.

FIG. 3 illustrates an example of a process for forming a dental appliance according to a number of embodiments of the present disclosure. The embodiment of FIG. 3 can include a virtual dental appliance and/or a physical dental appliance, in various embodiments.

As illustrated by the embodiment of FIG. 3, the dental appliance can include a removable shell 302, a first portion of an arch element 304, and a second portion of the arch element 306. The removable shell 302 can include a number of cavities formed therein, wherein the number of cavities are shaped to receive the number of teeth of the patient. The removable shell 302, as illustrated in FIG. 3, can include a virtual removable shell, a physical removable shell, and/or material to be thermoformed over a dental model (e.g., as discussed further herein).

The first portion of the arch element 304 can include a virtual first portion and/or a physical first portion, in various embodiments. The first portion of the arch element 304 can be formed of a material using a virtual model of the surface of the mouth of the patient and a virtual model of the number of teeth of the patient (e.g., the virtual and/or physical model of the lower jaw 318). The first portion of the arch element 304 can be wider than an arch width of the number of teeth of the first jaw of the patient, specific to a stage of the treatment plan, and/or shaped to substantially follow contours of a surface of the patient (e.g., floor of the mouth).

The model of the lower jaw 318, as illustrated in FIG. 3, can include a virtual model of a surface of the mouth of the patient including a virtual model of the number of teeth of patient. The virtual model (e.g., the model of the lower jaw 318) can be used to print and/or mill the first portion of the arch element.

Alternatively and/or in addition, the model of the lower jaw 318 can include a physical set of molded teeth. A physical set of molded teeth can be created, for instance, utilizing a virtual model of the surface of the mouth and/or the teeth of the patient.

The removable shell 302 can be formed over a physical set of molded teeth, in various embodiments. The removable shell 302 can include the number of cavities and a second portion of the arch element 306. The second portion of the arch element 306 can be formed concurrently with and/or of the same material as the cavities, for instance, using the model of the lower jaw 318. The material forming the first portion of the arch element 304 can be more rigid than the material forming the second portion of the arch element 306.

The first portion of the arch element 304 can be connected to the second portion of the arch element 306 to form a dental appliance. For example, the first portion of the arch element 304 can be placed within the physical set of molded teeth (e.g., the model of the lower jaw 318). An agent can be added to the second portion of the arch element. The first portion of the arch element 304 and the second portion of the arch element 306 can be connected as the removable shell 302 is thermoformed over the set of molded teeth. That is, the first portion of the block element 304 can be encapsulated in the set of molded teeth and can be adhered to the second portion of the arch element 306 utilizing an agent.

Alternatively, the first portion of the arch element 304 can be connected to the second portion of the arch element 306 subsequent to forming the first portion of the arch element 304 and the removable shell 302. For instance, the removable shell 302 can be thermoformed over the physical set of molded teeth. Subsequently, the first portion of the arch element 304 can be adhered to the second portion of the arch element 306. The portions of the arch element 304, 306 can be adhered using an agent or through means not requiring an agent (such as ultrasonic welding), for instance.

Figure 4:
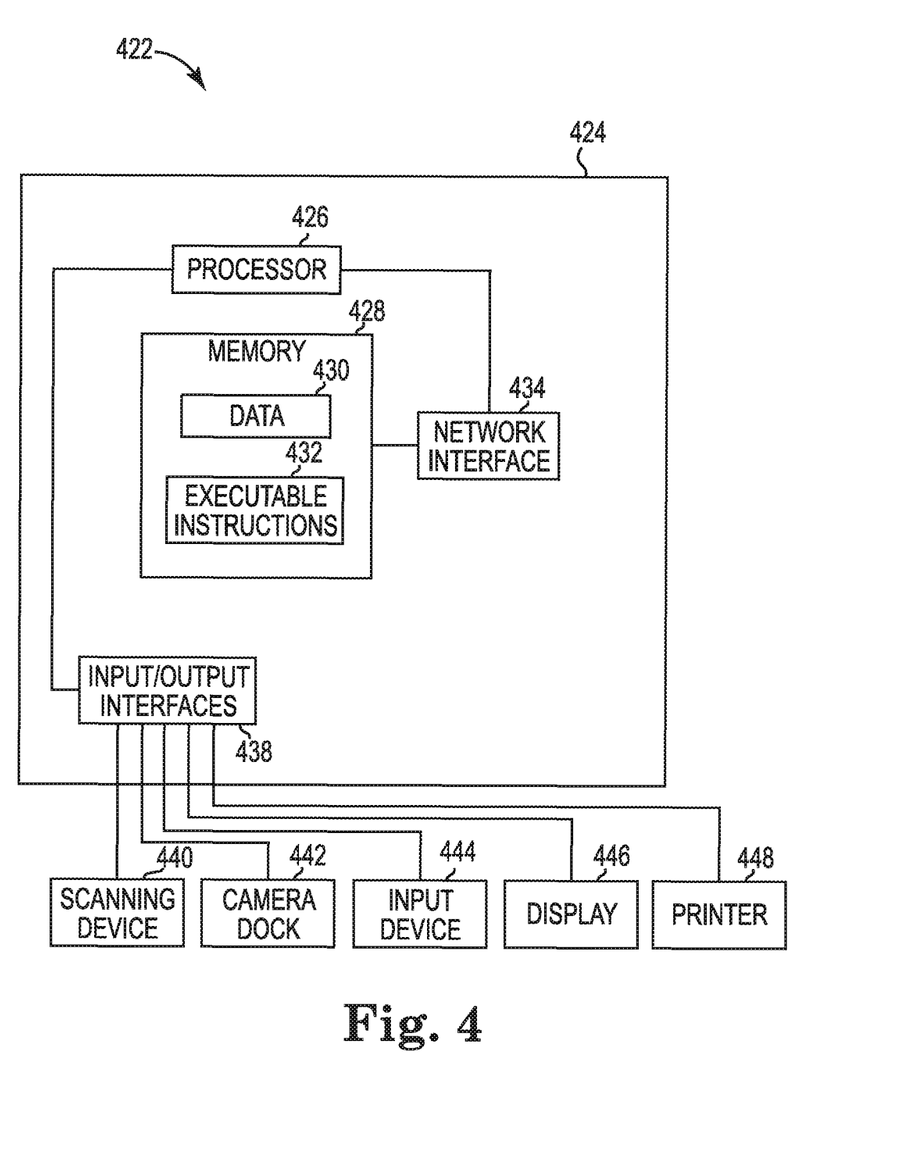
FIG. 4 illustrates an example computing device readable medium having executable instructions that can be executed by a processor to perform a method according to one or more embodiments of the present disclosure.

FIG. 4 illustrates an example computing device readable medium having executable instructions that can be executed by a processor to perform a method according to one or more embodiments of the present disclosure. For instance, a computing device 424 can have a number of components coupled thereto. The computing device 424 can include a processor 426 and a memory 428. The memory 428 can have various types of information including data 430 and executable instructions 432, as discussed herein.

The processor 426 can execute instructions 432 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 428 and/or the processor 426 may be located on the computing device 424 or off the computing device 424, in some embodiments. As such, as illustrated in the embodiment of FIG. 4, the computing device 424 can include a network interface 434. Such an interface 434 can allow for processing on another networked computing device, can be used to obtain information about the patient, and/or can be used to obtain data and/or executable instructions for use with various embodiments provided herein.

As illustrated in the embodiment of FIG. 4, the computing device 424 can include one or more input and/or output interfaces 438. Such interfaces 438 can be used to connect the computing device 424 with one or more input and/or output devices 440, 442, 444, 446, 448.

For example, in the embodiment illustrated in FIG. 4, the input and/or output devices can include a scanning device 440, a camera dock 442, an input device 444 (e.g., a mouse, a keyboard, etc.), a display device 446 (e.g., a monitor), a printer 448, and/or one or more other input devices. The input/output interfaces 438 can receive executable instructions and/or data, storable in the data storage device (e.g., memory), representing a virtual dental model of a patient's dentition.

In some embodiments, the scanning device 440 can be configured to scan one or more physical dental models of a patient's dentition. In one or more embodiments, the scanning device 440 can be configured to scan the patient's dentition and/or dental appliance directly. The scanning device 440 can be configured to input data into the computing device 424.

In some embodiments, the camera dock 442 can receive an input from an imaging device (e.g., a 2D or 3D imaging device) such as a virtual camera, a printed photograph scanner, and/or other suitable imaging device. The input from the imaging device can, for example, be stored in memory 428.

The processor 426 can execute instructions to provide a visual indication of a treatment plan, a dental appliance, and/or a portion of an arch element on the display 446. The computing device 424 can be configured to allow a treatment professional or other user to input treatment goals. Input received can be sent to the processor 426 as data 430 and/or can be stored in memory 428.

Such connectivity can allow for the input and/or output of data and/or instructions among other types of information. Some embodiments may be distributed among various computing devices within one or more networks, and such systems as illustrated in FIG. 4 can be beneficial in allowing for the capture, calculation, and/or analysis of information discussed herein.

The processor 426, in association with the data storage device (e.g., memory 428), can be associated with the data 430. The processor 426, in association with the memory 428, can store and/or utilize data 430 and/or execute instructions 432 for designing a virtual appliance for a specific stage of a treatment plan and/or a series of virtual appliances for a treatment plan. Such data can include the virtual dental model and/or virtual model of a surface of a patient's mouth (e.g., palate and/or floor of the mouth).

The processor 426 coupled to the memory 428 can cause the computing device 424 to perform a method including, for example, providing a virtual model of a dental appliance having a shell configured to reposition a number of teeth of a patient. The virtual model of the dental appliance can include a second portion of an arch element. In various embodiments of the present disclosure, the processor 426 coupled to the memory 428 can cause the computing device 424 to perform the method including providing a virtual model of a first portion of an arch element. The virtual model of the dental appliance can, in some embodiments, be used to create a physical dental appliance.

The first portion and the second portion of the arch element can be wider than the arch width of the number of teeth of the first jaw of the patient. For instance, the arch element can be shaped to substantially follow contours of the palate of the patient and/or the floor of the mouth of the patient, in some embodiments. The palatal contour in the model can be raised in order to result in a uniform relief gap between the appliance and the actual contour of the palate. The physical first portion can be formed of a material that is more rigid than the material forming the second portion.

In some embodiments, in order to direct force from the arch element to other portions of the shell, a more rigid material may be applied between the arch element and other portions of the shell (e.g., a rigid material is applied over and/or under the shell material or encapsulated within layers of shell material). Additionally, the rigid material used to form the arch element and/or force directing portions can be reinforced by a reinforcement material (e.g., a metallic sheet or wire material provided to the second material).

Figure 5:
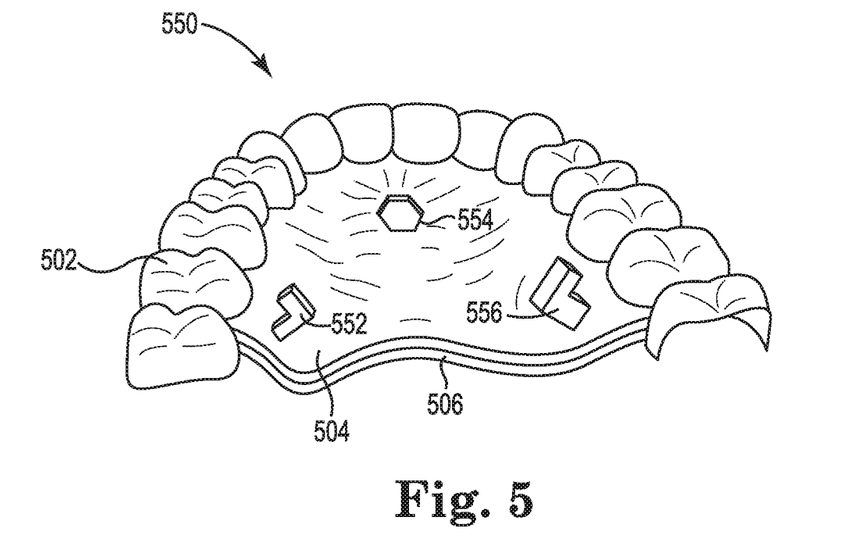
FIG. 5 illustrates an example of an appliance for expanding an arch of a patient having features provided on the palate surface according to a number of embodiments of the present disclosure.

FIG. 5 illustrates an example of an appliance 550 for expanding an arch of a patient according to a number of embodiments of the present disclosure. The appliance 550, as illustrated in FIG. 5, can include an appliance to be placed over an upper dentition of a patient.

The appliance 550 can include removable shell 502 formed of a first material having a number of cavities formed therein. The number of cavities can be shaped to receive teeth of the patient. An arch element can extend from the removable shell 502 in a lingual direction and across an arch width of the removable shell 502.

The arch element can be formed of the first material 506 and a second material 504 that is a different in at least one material property than the first material. For instance, as illustrated by FIG. 5, the arch element can be formed for a first layer of the first material 506 and a second layer of the second material 504. The second material 504 can include a material with at least one differing material property than the first material 506, for example.

The arch element can be designed to expand an arch of the teeth of the patient. For instance, the arch element (e.g., the first material 506 and the second material 504) can have a width that is wider than an arch width of the teeth of patient. The width can be specific to a stage of a treatment plan, for example. The arch element with a width wider than an arch width of the patient can apply a force to at least a portion of the number of teeth in a transverse direction to expand the arch of teeth of the patient. For example, the arch element can apply a force to the posterior teeth of the patient.

As illustrated by the embodiment of FIG. 5, in some embodiments, an appliance 550 can include a number of features 552, 554, 556. The number of features 552, 554, 556 can include a hollowed out portion of the first material 504 (e.g., an opening and/or hole in the first material 504).

In such an embodiment, interlocking the first portion of an arch element formed of a first material 504 to the second portion of the arch element formed of a second material 506 to form the dental appliance 550 can include thermoforming the removable shell 502 over the set of molded teeth (e.g., a physical set of molded teeth) with the first portion of the arch element (e.g., the first material 506) placed within the set of molded teeth. The thermoformed material (e.g., the second material 504) can surround the number of features 552, 554, 556 to physically connect the first portion of the arch element to the first portion of the arch element. These features confer the benefit of connecting the two components of the appliance together; they also have the benefit of altering the physical properties of the appliance due to changes in rigidity due to corrugation.

Figure 6:
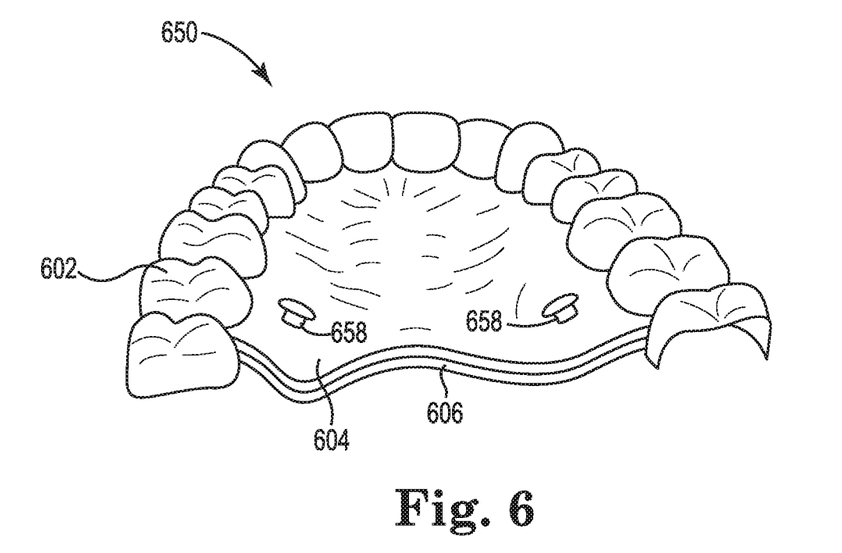
FIG. 6 illustrates another example of an appliance for expanding an arch of a patient having features provided on the palate surface according to a number of embodiments of the present disclosure.

FIG. 6 illustrates another example of an appliance for expanding an arch of a patient having features provided on the palatal surface according to a number of embodiments of the present disclosure. As with the appliance of FIG. 5, the appliance 650, as illustrated in FIG. 6, can include an appliance to be placed over an upper dentition of a patient.

The appliance 650 includes a removable shell 602 formed of a first material having a number of cavities formed therein. The arch element extends from the removable shell 602 in a lingual direction and across an arch width of the removable shell 602. The arch element is formed of the first material 606 and a second material 604 that is a different in at least one material property than the first material.

As illustrated by the embodiment of FIG. 6, in some embodiments, an appliance 650 can include a number of features 658. The number of features 658 can include a button style feature with a top portion and a trunk portion that is smaller than the top portion in at least one dimension.

In such an embodiment, interlocking the first portion of an arch element formed of a first material 604 to the second portion of the arch element formed of a second material 606 to form the dental appliance 650 can include thermoforming the removable shell 602 over the set of molded teeth (e.g., a physical set of molded teeth) with the first portion of the arch element (e.g., the first material 606) placed within the set of molded teeth. The thermoformed material (e.g., the second material 604) can surround the number of features 658 to physically connect the first portion of the arch element to the first portion of the arch element. As with the features of FIG. 5, these features confer the benefit of connecting the two components of the appliance together; they also have the benefit of altering the physical properties of the appliance due to changes in rigidity due to corrugation.

Figure 7:
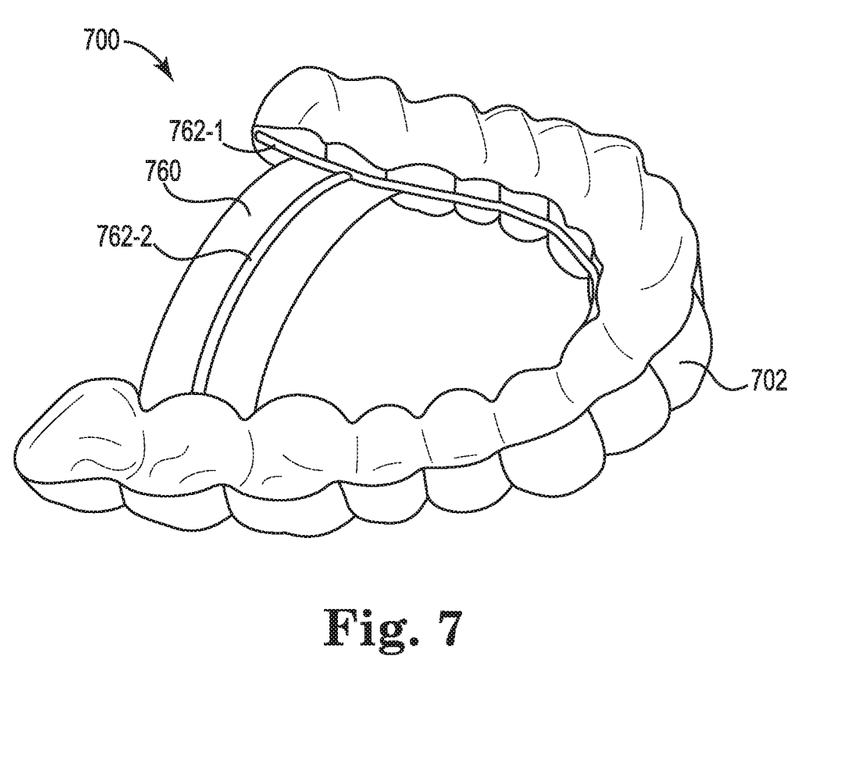
FIG. 7 illustrates another example of an appliance for expanding an arch of a patient having raised features thereon according to a number of embodiments of the present disclosure.

FIG. 7 illustrates another example of an appliance for expanding an arch of a patient having raised features thereon according to a number of embodiments of the present disclosure. In this embodiment an appliance 700 includes a shell portion 702 with a tab element 760 that spans across the palate between the two sides of the shell 702.

The tab element 760 can be designed to expand an arch of the teeth of the patient. For instance, as with the arch element of FIG. 5, the tab element can have a width that is wider than an arch width of the teeth of patient. The width can be specific to a stage of a treatment plan, for example. The tab element with a width wider than an arch width of the patient can apply a force to at least a portion of the number of teeth in a transverse direction to expand the arch of teeth of the patient. For example, the tab element can apply a force to the posterior teeth of the patient.

In addition, the embodiment of FIG. 7 includes raised portions that are used to reinforce portions of the appliance. For example, raised elements 762-1 and 762-2 have been positioned to provide added force to the shell 702 and the tab element 760. These elements can have any suitable cross-sectional shape (for example, a half circular cross section) and can be of the same material or a different material than the shell and/or the tab element.

Figure 8:
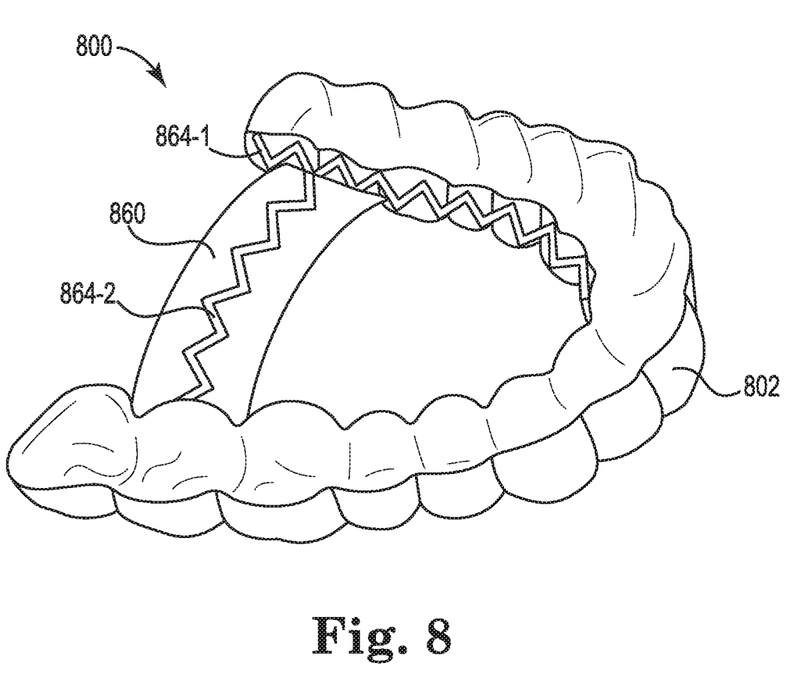
FIG. 8 illustrates another example of an appliance for expanding an arch of a patient having zig-zag features thereon according to a number of embodiments of the present disclosure.

FIG. 8 illustrates another example of an appliance for expanding an arch of a patient having zig-zag features thereon according to a number of embodiments of the present disclosure. The embodiment of FIG. 8 includes illustrates an appliance 800 with a shell 802 and a tab element 860. In this embodiment, the raised elements 864-1 and 864-2 are shaped in a wave (rounded transitions) or zig-zag, (angled transitions, as shown in FIG. 8). Such features can provide force or reinforcement in transverse directions to a direction of elongation of the shell and/or the tab element. Such features, as are shown in FIGS. 7 and 8 can be provided along the entire length of the shell and/or tab element or along a portion thereof. As illustrated in the embodiments of FIGS. 7 and 8, some embodiments can have a palatal component (e.g., tab element) that is offset from the palatal surface of the patient (having a space between the tab element surface and the palatal surface). Such embodiments, minimize the need for the doctor to make adjustments to the appliance.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An appliance comprising:
   a removable shell having a number of cavities formed therein, wherein the number of cavities are shaped to receive teeth of a patient; and
   a first arch element extending from the removable shell in a lingual direction and continuing uninterrupted across the arch width of the removable shell from a first side of the removable shell to a second side of the removable shell and designed to expand an arch of the teeth of the patient, wherein the first arch element has a width specific to a stage of a treatment plan and includes at least one raised reinforcement feature that extends from the removable shell in a lingual direction and continuing uninterrupted across the arch width of the removable shell from the first side of the removable shell to the second side of the removable shell.

2. The appliance of claim 1, wherein the first arch element is a tab element.

3. The appliance of claim 2, wherein the tab element applies a force to a portion of the teeth of the patient.

4. The appliance of claim 3, wherein the portion of the teeth of the patient are posterior teeth of the patient.

5. A system, comprising:
   a first appliance, of a series of appliances designed to incrementally implement a treatment plan, comprising a first shell having a plurality of cavities therein designed to receive teeth of a first jaw, wherein the first appliance includes a first arch element, extending therefrom in a lingual direction and continuing uninterrupted across an arch width of the first shell from a first side of the first shell to a second side of the first shell and designed to expand an arch of the teeth of a patient, wherein the first arch element includes at least one raised feature and the first arch element has a first width specific to a first stage of the treatment plan; and
   a second appliance, of the series of appliances, comprising a second shell having a plurality of cavities therein designed to receive teeth of the first jaw, wherein the second appliance includes a second arch element, wherein second arch element has a second width specific to a second stage of the treatment plan and wherein the second width is different than the first width.

6. The system of claim 5, wherein the at least one raised feature is designed to make the first arch element more rigid.

7. The system of claim 5, wherein the at least one raised feature is formed of the same material as the first shell.

8. The system of claim 5, wherein the at least one raised feature is formed of the same material as the first arch.

9. The system of claim 5, wherein the at least one raised feature is formed of a different material than the first shell and the first arch.

10. The system of claim 5, wherein the at least one raised feature cross-sectional shape is a half circle.

11. A method of forming a dental appliance, comprising:
   forming a first portion of an arch element using a virtual model of a palate of a patient and a virtual model of a number of teeth of the patient, wherein the first portion of the arch element includes at least one raised feature, is wider than an arch width of the number of teeth of a first jaw of the patient, and specific to a stage of a treatment plan;
   forming a removable shell over a set of molded teeth, wherein the removable shell includes:
      a number of cavities formed therein, wherein the number of cavities are shaped to receive the number of teeth of the patient; and
      a second portion of the arch element extending from the first portion of the arch element and continuing uninterrupted across the arch width of the removable shell from a first side of the removable shell to a second side of the removable shell; and
   connecting the first portion of the arch element to the second portion of the arch element to form the dental appliance, wherein the arch element is designed to provide a force to at least a portion of the number of teeth in a transverse direction to expand the arch of teeth of the first jaw of the patient.

12. The method of claim 11, wherein forming the first portion of the arch element includes forming the at least one raised feature in the shape of a wave.

13. The method of claim 11, wherein forming the first portion of the arch element includes forming the at least one raised feature in the shape of a zig-zag.

14. The method of claim 11, wherein forming the first portion of the arch element includes forming the at least one raised feature as an elongated element that is straight in the direction of elongation.

15. The method of claim 11, wherein forming the first portion of the arch element includes forming the at least one raised feature in a position to provide added force to the removable shell.

16. An appliance comprising:
a removable shell having a number of cavities formed therein, wherein the number of cavities are shaped to receive teeth of a patient; and
a first arch element extending from the removable shell in a lingual direction and continuing uninterrupted across the arch width of the removable shell from a first side of the removable shell to a second side of the removable shell and designed to expand an arch of the teeth of the patient, wherein the first arch element has a width specific to a stage of a treatment plan and includes at least one reinforcement feature and at least one button style feature including a top portion and a trunk portion, wherein the trunk portion is smaller than the top portion in at least one dimension.

17. The appliance of claim 16, wherein the button style feature interlocks the first arch element with a second arch element.

* * * * *